(12) United States Patent
Jeong et al.

(10) Patent No.: US 9,463,040 B2
(45) Date of Patent: Oct. 11, 2016

(54) DEVICE FOR FIXING JOINT STRUCTURE

(71) Applicant: Chang Wook Jeong, Seoul (KR)

(72) Inventors: Chang Wook Jeong, Seoul (KR); Hyung Tae Kim, Seoul (KR)

(73) Assignee: MOVASU, INC., Seoul (KR)

( * ) Notice: Subject to any disclaimer, the term of this patent is extended or adjusted under 35 U.S.C. 154(b) by 0 days.

(21) Appl. No.: 14/422,153

(22) PCT Filed: Aug. 14, 2013

(86) PCT No.: PCT/KR2013/007347
§ 371 (c)(1),
(2) Date: Apr. 15, 2015

(87) PCT Pub. No.: WO2014/027846
PCT Pub. Date: Feb. 20, 2014

(65) Prior Publication Data
US 2015/0230815 A1    Aug. 20, 2015

(30) Foreign Application Priority Data

Aug. 14, 2012    (KR) .................. 10-2012-0089119

(51) Int. Cl.
*G05G 5/02*        (2006.01)
*A61B 17/29*       (2006.01)
*A61B 19/00*       (2006.01)
*A61B 17/00*       (2006.01)

(52) U.S. Cl.
CPC .............. *A61B 17/29* (2013.01); *A61B 19/22* (2013.01); *G05G 5/02* (2013.01); *A61B 2017/003* (2013.01); *A61B 2017/2927* (2013.01); *Y10T 74/20636* (2015.01)

(58) Field of Classification Search
CPC ................ A61B 17/29; A61B 19/22; A61B 2017/2919; A61B 2017/2927; A61B 2017/003; G05G 5/02; Y10T 74/20636; Y10T 74/20672
See application file for complete search history.

(56) References Cited

U.S. PATENT DOCUMENTS 5,954,179 A * 9/1999 Osborn .................. B60T 1/005
                                                        192/219.5
5,954,678 A    9/1999 Cruz
(Continued)

FOREIGN PATENT DOCUMENTS

EP    2743042 A2 *  6/2014  .......... A61B 17/062
JP    2008-093432 A    4/2008
(Continued)

OTHER PUBLICATIONS

International Search Report for the International Application No. PCT/KR2013/007347, Korean Intellectual Property Office, Nov. 27, 2013.

*Primary Examiner* — Adam D Rogers
(74) *Attorney, Agent, or Firm* — Mayer Brown LLP; Hyunho Park

(57) ABSTRACT

The present invention relates to a device for fixing a joint structure. The device for fixing a joint structure, according to one aspect of the present invention, comprises: a first slider for fixing a first directional joint movement state of a joint structure that includes a first joint element and a second joint element; a first locking member included in the first slider; and a first corresponding locking member which operates relative to the first locking member and blocks a forward directional movement and a backward directional movement of the first slider.

7 Claims, 4 Drawing Sheets

(56) References Cited

U.S. PATENT DOCUMENTS

| | | | | |
|---|---|---|---|---|
| 7,780,054 B2* | 8/2010 | Wales | ............. | A61B 17/00234 227/175.1 |
| 7,963,976 B2* | 6/2011 | Goldfarb | ................ | A61B 17/02 600/141 |
| 2011/0087269 A1* | 4/2011 | Stokes | ................... | A61B 17/29 606/206 |
| 2015/0173747 A1* | 6/2015 | Baxter, III | ....... | A61B 17/07207 227/177.1 |

FOREIGN PATENT DOCUMENTS

| | | |
|---|---|---|
| KR | 10-0563709 B1 | 3/2006 |
| KR | 10-2010-0104125 A | 9/2010 |

* cited by examiner

DEVICE FOR FIXING JOINT STRUCTURE

FIELD OF THE INVENTION

The present invention relates to an apparatus for fixing a joint structure.

BACKGROUND

Joint motion may refer to the movement of at least one of two or more interconnected (mechanical) elements relative to the other ones. Such joint motion may be observed in various forms from human arms or legs to robotic arms of an industrial robot.

In some cases, instruments (particularly surgical instruments) capable of joint motion are required to fix the joint motion state of the mechanical elements thereof. In order to fix the joint structure, there have been conventionally used devices or components configured with balls and sockets, which mainly rely upon the surface friction between two mechanical elements, as disclosed in Korean Patent Application No. 2011-3192 of the applicant(s) (the contents of which are to be regarded as being incorporated herein by reference in its entirety); a construction for fixing the motion state of a joint by fixing only wires for controlling the joint motion, as disclosed in Korean Patent Application No. 2010-115152 of the applicant(s) (the contents of which are to be regarded as being incorporated herein by reference in its entirety); or joint fixing constructions as disclosed in Korean Patent Application Nos. 2008-51248, 2008-61894, 2008-79126, 2008-90560, 2011-26243, 2011-29771 and the like of the applicant(s) (the contents of which are to be regarded as being incorporated herein by reference in its entirety). However, such devices, components, constructions or the like have often been inadequate to efficiently achieve sufficiently firm fixation.

Herein, the inventor(s) thus present a novel apparatus for fixing a joint structure.

SUMMARY OF THE INVENTION

One object of the present invention is to solve all the above problems in prior art.

Another object of the invention is to provide a novel joint structure fixing apparatus having good fixing performance.

Yet another object of the invention is to provide an apparatus capable of effectively fixing a joint structure without relying upon surface friction.

According to one aspect of the invention to achieve the objects as described above, there is provided a joint structure fixing apparatus, comprising: a first slider to fix a first directional joint motion state of a joint structure including a first joint element and a second joint element; a first lock member included in the first slider; and a first counterpart lock member to act on the first lock member to block forward and backward directional movements of the first slider.

In addition, there may be further provided other configurations according to the technical idea of the invention.

According to the invention, there is provided a novel joint structure fixing apparatus having good fixing performance.

According to the invention, there is provided an apparatus capable of effectively fixing a joint structure without relying upon surface friction.

DETAILED DESCRIPTION OF THE PREFERRED EMBODIMENTS

Figure 1:
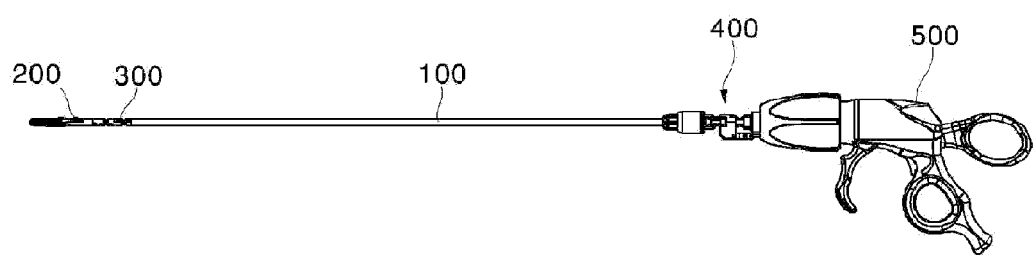
FIG. 1 is a diagram illustrating the overall appearance of a minimally invasive surgical instrument comprising a joint structure fixing apparatus according to one embodiment of the invention.

In the following detailed description of the present invention, references are made to the accompanying drawings that show, by way of illustration, specific embodiments in which the invention may be practiced. These embodiments are described in sufficient detail to enable those skilled in the art to practice the invention. It is to be understood that the various embodiments of the invention, although different from each other, are not necessarily mutually exclusive. For example, specific shapes, structures and characteristics described herein may be implemented as modified from one embodiment to another without departing from the spirit and scope of the invention. Furthermore, it shall be understood that the locations or arrangements of individual elements within each embodiment may also be modified without departing from the spirit and scope of the invention. Therefore, the following detailed description is not to be taken in a limiting sense, and the scope of the invention is to be taken as encompassing the scope of the appended claims and all equivalents thereof. In the drawings, like reference numerals refer to the same or similar elements throughout the several views.

Hereinafter, preferred embodiments of the present invention will be described in detail with reference to the accompanying drawings to enable those skilled in the art to easily implement the invention.

Meanwhile, it should be understood that the term "connection" herein encompasses a direct connection or an indirect connection (i.e., via separate components) between mechanical or other types of components. For example, a connection between two rotating components may be a direct connection formed by the engagement of corresponding gear elements or the like, but may also be an indirect connection via a separate component such as a cable or a groove.

FIG. 1 is a diagram illustrating the overall appearance of a minimally invasive surgical instrument comprising a joint structure fixing apparatus according to one embodiment of the invention.

Reference will be made to FIG. 1. The minimally invasive surgical instrument may comprise a shaft 100; an end effector 200 being connected to one end of the shaft 100 to perform surgery by using surgical tools (not shown) or functioning itself as a surgical tool; a joint unit 300 to connect the shaft 100 and the end effector 200 and to provide the end effector 200 with joint functionality; a joint structure fixing apparatus 400 according to the invention; and a handling unit 500 being connected to the other end of the shaft 100 and capable of being held and manipulated by a user.

First, the shaft 100 may include a cavity therein to support and pass at least one wire or torque transmission member, in the same manner as those of the minimally invasive surgical instruments disclosed in the aforementioned Korean patent applications of the applicant(s). (The torque transmission member is mainly intended for the rolling motion of the end effector 200, while the shaft 100 may function itself as the torque transmission member in some cases.) The shaft 100 may comprise at least one segment as necessary. Further, the shaft 100 may comprise a bend in at least a part thereof.

Next, the end effector 200 may carry out joint motion, rolling motion, opening/closing motion and the like by the action of the at least one wire or torque transmission member passing from the handling unit 500 to the joint unit 300 via the shaft 100, in the same manner as those of the minimally invasive surgical instruments disclosed in the aforementioned Korean patent applications of the applicant(s). The tip of the end effector 200 may be implemented in the form of a clamp, a grasper, a pair of scissors, a stapler, a needle holder, a hook-type electrode or the like.

Next, the joint unit 300 may act together with the at least one wire or torque transmission member to allow the end effector 200 to carry out joint motion, rolling motion and the like, in the same manner as those of the minimally invasive surgical instruments disclosed in the aforementioned Korean patent applications of the applicant(s).

Finally, the handling unit 500 may control the joint motion, rolling motion, opening/closing motion and the like of the end effector 200 according to the user's manipulation, in the same manner as those of the minimally invasive surgical instruments disclosed in the aforementioned Korean patent applications of the applicant(s). To allow for such control, the at least one wire or torque transmission member may be connected to the handling unit 500. Meanwhile, as illustrated, another joint unit (i.e., a proximal joint unit), which may carry out joint motion to cause corresponding joint motion in the joint unit 300, and the joint structure fixing apparatus 400 according to the invention, which may fix the joint motion state of the joint unit, may be provided between the handling unit 500 and the shaft 100. The joint structure fixing apparatus 400 will be described in detail below.

Figure 2:
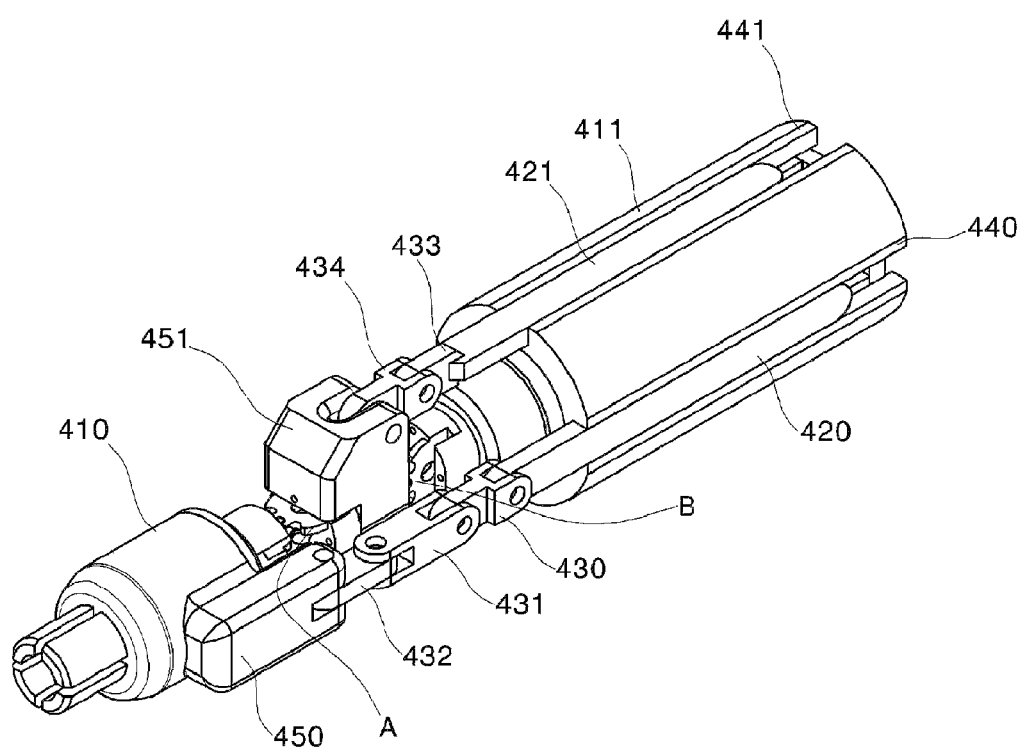
FIG. 2 is a detailed diagram illustrating a joint structure fixing apparatus 400 according to one embodiment of the invention.

FIG. 2 is a detailed diagram illustrating the joint structure fixing apparatus 400 according to one embodiment of the invention.

Reference will be made to FIG. 2. In order to fix a joint structure formed by a first joint element 410 and a second joint element 411, the joint structure fixing apparatus 400 may comprise a first slider 420 and a second slider 421; lock members included in each of the first slider 420 and the second slider 421; other lock members to engage with the lock members to implement fixation (the lock members will be further described below with reference to FIG. 3); a first rail 440 and a second rail 441 to respectively guide the slides of the first slider 420 and the second slider 421; and a first link set 430, 431, 432 to connect the first joint element 410 and the first slider 420, and a second link set 433, 434 to connect the second joint element 411 and the second slider 421.

First, the first joint element 410 and the second joint element 411 will be discussed. One of the first joint element 410 and the second joint element 411 may move in a pitch direction or a yaw direction in relation to the other (i.e., may carry out joint motion). According to one embodiment of the invention, the relative movement of the first joint element 410 and the second joint element 411 may cause joint motion of the joint unit 300. In a specific example, the second joint element 411 may move in a pitch direction or a yaw direction in relation to the first joint element 410 so that the joint motion of the joint unit 300 may be caused by the action of a joint motion control wire (not shown) of which one end may be fixed to the second joint element 411 or another element moving therewith (not shown) and the other end may be fixed to the joint unit 300. The first joint element 410 and the second joint element 411 may be connected to each other via a joint part A for relative yaw directional movement (which may be a joint part similar to 300 in FIG. 3 of Korean Patent Application No. 2008-51248 of the applicant(s), for example) or a joint part B for relative pitch directional movement (which may be a joint part similar to 200 in FIG. 3 of Korean Patent Application No. 2008-51248 of the applicant(s), for example).

The first slider 420 and the second slider 421 will be discussed. The first slider 420 may slide along the first rail 440 only in forward and backward directions, and likewise the second slider 421 may slide along the second rail 441 only in forward and backward directions. The first rail 440 and the second rail 441 may be respectively shaped as illustrated in FIG. 2, so that the first slider 420 and the second slider 421 may slide in the corresponding grooves. The configurations of the first slider 420 and the second slider 421 or the first rail 440 and the second rail 441 may be diversely changed as long as the first slider 420 and the second 421 may slide without much wobble.

Next, the first link set 430, 431, 432 and the second link set 433, 434 will be discussed. For the relative yaw directional movement of the first joint element 410 and the second joint element 411, the first link set 430, 431, 432, which may act together with the first slider 420, may be provided to fix the state of the movement or release the fixation. The first link set 430, 431, 432 may comprise a plurality of (e.g., three) links. Each of the links may be a known Y-shaped link, a known U-shaped link composite, a known planar link or the like, as illustrated in FIG. 2. Meanwhile, the first link set 430, 431, 432 may be fixed and connected to a first link fixing member 450 of which one end may be attached to the first slider 420 and the other end may be attached to the first joint element 410. The first joint element 410 or the second joint element 411 may move in a pitch direction by the action of the first link 430 and the second link 431 of the first link set 430, 431, 432, and may move in a yaw direction by the action of the second link 431 and the third link 432 of the first link set 430, 431, 432. Particularly, in the latter case, the first slider 420 may slide in forward and backward directions. Similarly, for the relative pitch directional movement of the first joint element 410 and the second joint element 411, the second link set 433, 434, which may act together with the second slider 421, may be provided to fix the state of the movement or release the fixation. The second link set 433, 434 may comprise a plurality of (e.g., two) links. Each of the links may be a known planar link, a known Y-shaped link or the like, as illustrated in FIG. 2. Meanwhile, the second link set 433, 434 may be fixed and connected to a second link fixing member 451 of which one end may be attached to the second slider 421 and the other end may be attached to the portion where the joint part A and the joint part B are connected. The first joint element 410 or the second joint element 411 may move in a pitch direction by the action of the first link 433 and the second link 434 of the second link set 433, 434. In this case, the second slider 421 may slide in forward and backward directions.

Figure 3:
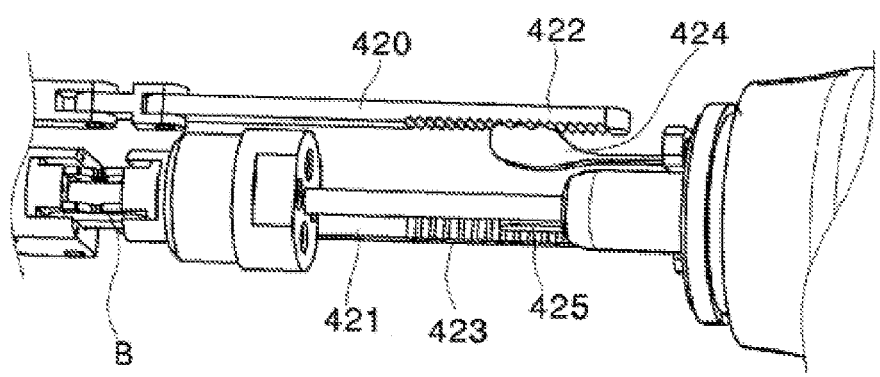
FIG. 3 is a diagram illustrating the appearance of a first lock member 422 of a first slider 420 and a first counterpart lock member 424 outside thereof according to one embodiment of the invention.

FIG. 3 is a diagram illustrating the appearance of a first lock member 422 of the first slider 420 and a first counterpart lock member 424 outside thereof according to one embodiment of the invention.

Figure 4:
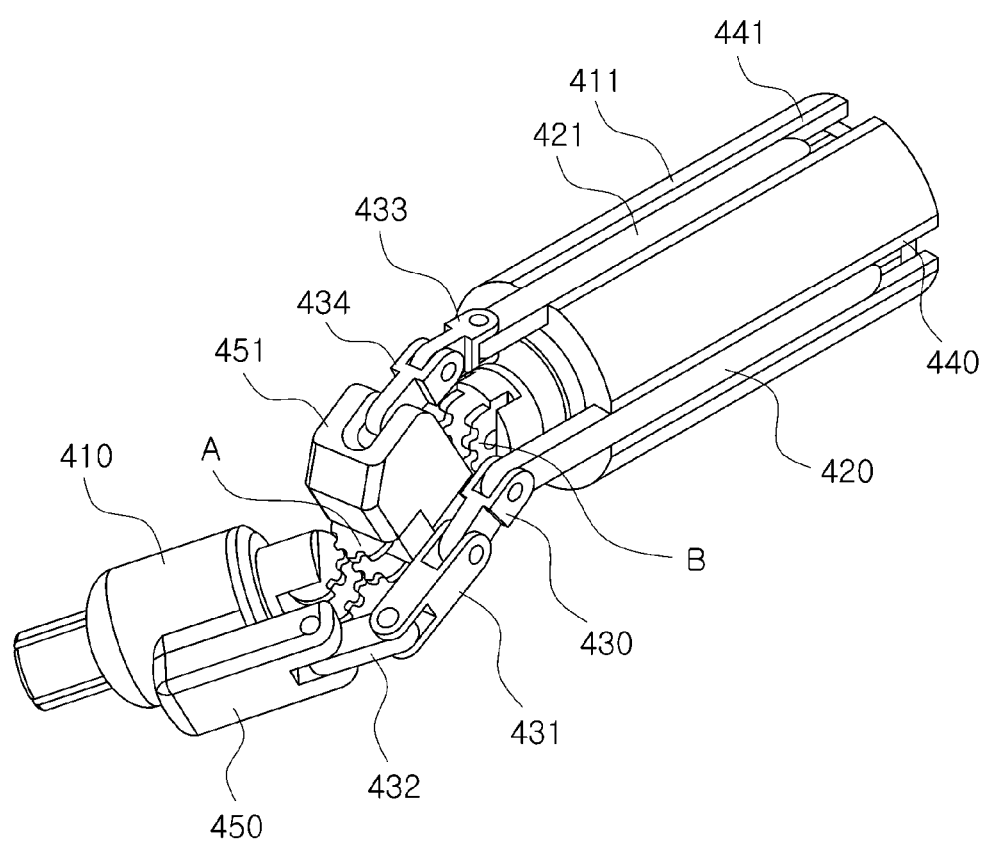
FIG. 4 is another detailed diagram illustrating the joint structure fixing apparatus 400 according to one embodiment of the invention.

Reference will be made to FIG. 3. The first slider 420 may include a first lock member 422 on the inner side surface thereof, and correspondingly, a first counterpart lock member 424 outside thereof may also be provided. Therefore, a user may operate the first counterpart lock member 424 to fix the first slider 420 so that it may not slide in forward and backward directions, when the joint formed by the first joint element 410 and the second joint element 411, and further the joint of the joint unit 300 which may be interlocked with the former one, are required to be fixed in a yaw direction. (In this case, the motion state of the first link set 430, 431, 432 may also be fixed.) To this end, the first lock member 422 may include a plurality of serrations, and the first counterpart lock member 424 may be shaped such that it may be fitted into a portion of the serrations. Meanwhile, the second slider 421 may also be provided with a second lock member 423 and a second counterpart lock member 425 so that the second slider 421 may be fixed in a pitch direction (and the motion state of the second link set 433, 434 may be fixed.) Therefore, a user may fix both the first slider 420 and the second slider 421 as necessary, thereby completely fixing the motion state of the joint formed by the first joint element 410 and the second joint element 411, and further the joint motion state of the joint unit 300 which is interlocked therewith. Accordingly, for example, the motion state of the joint formed by the first joint element 410 and the second joint element 411 may be firmly fixed by the first link set 430, 431, 432 and the second link set 433, 434, which hold the joint parts A, B therearound as illustrated in FIG. 4, as the first slider 420 and the second slider 421 are fixed.

Meanwhile, in order to facilitate understanding of the invention, it has been mainly described above that the first slider 420 and the related elements, which may independently restrain the relative yaw directional movement of the first joint element 410 and the second joint element 411, are employed together with the second slider 421 and the related elements, which may independently restrain the relative pitch directional movement of the first joint element 410 and the second joint element 411. However, other configurations in which, for example, only one of the first slider 420 and the second slider 421 is employed, or three or more sliders not needing to independently restrain the relative pitch or yaw directional movement of the first joint element 410 and the second joint element 411 are employed together, may also be implemented by those skilled in the art, without limitation, according to the technical idea of the invention.

Although the present invention has been described in terms of specific items such as detailed elements as well as the limited embodiments and the drawings, they are only provided to help more general understanding of the invention, and the present invention is not limited to the above embodiments. It will be appreciated by those skilled in the art to which the present invention pertains that various modifications and changes may be made from the above description.

Therefore, the spirit of the present invention shall not be limited to the above-described embodiments, and the entire scope of the appended claims and their equivalents will fall within the scope and spirit of the invention.

Particularly, in view of the technical idea of the present invention, it will be apparent that instruments to which the invention is applied shall not be limited to surgical instruments.

What is claimed is:

1. A joint structure fixing apparatus, comprising:
   a first slider to fix a first directional joint motion state of a joint structure including a first joint element and a second joint element;
   a first lock member included in the first slider;
   a first counterpart lock member to act on the first lock member to block forward and backward directional movements of the first slider;
   a second slider to fix a second directional joint motion state of the joint structure;
   a second lock member included in the second slider; and
   a second counterpart lock member to act on the second lock member to block forward and backward directional movements of the second slider,
   wherein the first slider is connected to the first joint element via a first link set.

2. The joint structure fixing apparatus of claim 1, wherein there are a first joint part and a second joint part between the first joint element and the second joint element, and
   the second slider is connected between the first joint part and the second joint part via a second link set.

3. The joint structure fixing apparatus of claim 2, wherein the second link set comprises only a link for the second directional joint motion.

4. The joint structure fixing apparatus of claim 1, wherein the first link set comprises a link for the first directional joint motion and a link for the second directional joint motion.

5. The joint structure fixing apparatus of claim 1, wherein the first slider or the second slider carries out sliding movement along a linear path on the second joint element.

6. The joint structure fixing apparatus of claim 1, wherein the first lock member or the second lock member includes a plurality of serrations.

7. The joint structure fixing apparatus of claim 6, wherein the first counterpart lock member or the second counterpart lock member is capable of being fitted into a corresponding portion of the plurality of serrations when in action.

* * * * *